US011403820B1

(12) United States Patent
Sargent et al.

(10) Patent No.: US 11,403,820 B1
(45) Date of Patent: Aug. 2, 2022

(54) PREDICTIVE RENDERING OF AN IMAGE

(71) Applicant: INTERNATIONAL BUSINESS MACHINES CORPORATION, Armonk, NY (US)

(72) Inventors: Dustin Michael Sargent, San Diego, CA (US); Hui Shen, San Diego, CA (US); Sun Young Park, San Diego, CA (US)

(73) Assignee: International Business Machines Corporation

( * ) Notice: Subject to any disclaimer, the term of this patent is extended or adjusted under 35 U.S.C. 154(b) by 0 days.

(21) Appl. No.: 17/198,792

(22) Filed: Mar. 11, 2021

(51) Int. Cl.
| | |
|---|---|
| G06T 15/00 | (2011.01) |
| G06T 19/00 | (2011.01) |
| H04L 43/08 | (2022.01) |
| G16H 30/40 | (2018.01) |

(52) U.S. Cl.
CPC ............. *G06T 19/00* (2013.01); *G16H 30/40* (2018.01); *H04L 43/08* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| | | |
|---|---|---|
| 7,515,156 B2 | 4/2009 | Tinker |
| 9,042,617 B1 | 5/2015 | Reicher |
| 9,808,708 B1* | 11/2017 | Wakeford ............. A63F 13/792 |
| 9,934,568 B2 | 4/2018 | Reicher |
| 10,431,180 B1 | 10/2019 | Sampath |
| 10,496,789 B2 | 12/2019 | Krotz |
| 10,607,735 B2 | 3/2020 | Bronkalla |
| 10,679,314 B2 | 6/2020 | Pronovost |
| 2006/0114254 A1* | 6/2006 | Day ....................... G06T 15/08 345/424 |
| 2006/0195507 A1* | 8/2006 | Baek ..................... H04L 67/322 709/203 |
| 2007/0252834 A1* | 11/2007 | Fay ........................ G06T 3/4092 345/428 |
| 2013/0083018 A1* | 4/2013 | Geisner .................. G06F 3/011 345/420 |
| 2015/0355772 A1* | 12/2015 | Hewitt .................. G16H 40/63 345/173 |

(Continued)

OTHER PUBLICATIONS

Abdellah, et al., "High Performance GPU-Based Fourier Volume Rendering," International Journal of Biomedical Imaging, Jan. 9, 2015, 13 pages, https://dx.doi.org/10.1155/2015/590727.

(Continued)

*Primary Examiner* — Anh-Tuan V Nguyen
(74) *Attorney, Agent, or Firm* — Steven M. Bouknight

(57) ABSTRACT

A method for preemptively generating and rendering a view of a computerized image is provided. The method may include determining rendering parameters for the computerized image by predicting an action to be performed on the computerized image, wherein the action modifies a view of the computerized image, and wherein the determined rendering parameters are based on the modified view of the computerized image. The method may further include preemptively rendering the view of the computerized image that is based on the determined rendering parameters before the action is performed on the computerized image.

20 Claims, 5 Drawing Sheets

(56) References Cited

U.S. PATENT DOCUMENTS

| | | | |
|---|---|---|---|
| 2016/0219325 A1* | 7/2016 | Chu | G06T 15/20 |
| 2017/0039701 A1* | 2/2017 | Fram | G06K 9/52 |
| 2017/0109935 A1* | 4/2017 | Loffler | G06F 3/011 |
| 2017/0344194 A1* | 11/2017 | Peterson | G06F 9/451 |
| 2018/0096494 A1* | 4/2018 | Zhou | G06T 19/003 |
| 2018/0260840 A1* | 9/2018 | Jeon | G06Q 30/0246 |
| 2019/0188535 A1 | 6/2019 | Chen | |
| 2019/0347689 A1* | 11/2019 | Bullock | G06Q 30/0277 |
| 2020/0159018 A1 | 5/2020 | Stafford | |
| 2020/0167999 A1 | 5/2020 | Schmit | |
| 2020/0184495 A1 | 6/2020 | Samarev | |
| 2020/0184708 A1 | 6/2020 | Petkov | |
| 2020/0203005 A1 | 6/2020 | Brigil | |
| 2021/0141515 A1* | 5/2021 | Wichary | G06F 3/04842 |

OTHER PUBLICATIONS

Chen, et al., "Learning To Predict 3D Objects With An Interpolation-Based Differentiable Renderer," arXiv:1908.01210v2[cs.CV], Nov. 21, 2019, 11 pages, https://arxiv.org/abs/1908.01210.

Gharibshah, et al., "Deep Learning For User Interest And Response Prediction In Online Display Advertising," Data Science and Engineering, Jan. 17, 2020, pp. 12-26, https://doi.org/10.1007/s41019-019-00115-y.

Heng, et al., "GPU-Based vol. Rendering for Medical Image Visualization," Proceedings of the 2005 IEEE, accessed Mar. 11, 2021, 4 pages, https://ieeexplore.ieee.org/stamp/stamp.jsp?tp&arnumber=1615635.

Lamberti, et al., "A Solution For Displaying Medical Data Models On Mobile Devices," ICSE 2005, accessed Mar. 11, 2021, 8 pages, https://www.semanticscholar.org/paper/A-solution-for-displaying-medical-data-models-on-Lamberti-Sanna/4d9ccb317e8fc2b6bdc46503693eebfe2aabcaea.

Mell et al., "The NIST Definition of Cloud Computing," National Institute of Standards and Technology, Special Publication 800-145, Sep. 2011, pp. 1-7.

Shi, et al., "A Real-Time Remote Rendering System For Interaction Mobile Graphics," ACM Transactions on Multimedia Computing, Communications, and Applications, Sep. 2012, 20 pages, https://doi.acm.org/10.1145/2348816.2348825.

Wheeler, et al., "Virtual Interaction and Visualization of 3D Medical Imaging Data With VTK And Unity," Healthcare Technology Letters, Aug. 2018, 7 pages, https://www.researchgate.net/publication/327182589.

* cited by examiner

PREDICTIVE RENDERING OF AN IMAGE

BACKGROUND

The present invention relates generally to the field of computing, and more specifically, to computer image rendering and viewing devices.

Generally, medical imaging refers to techniques and processes used to create images of various parts of the human body for diagnostic and treatment purposes within digital health. Specifically, medical imaging may be used to reveal internal structures hidden by the skin and bones, as well as to diagnose and treat disease. Medical imaging also establishes a database of normal anatomy and physiology to make it possible to identify different parts of the body as well as identify abnormalities in the body. The term, medical imaging, includes various radiological imaging techniques such as X-ray radiography, fluoroscopy, magnetic resonance imaging (MRI), medical ultrasonography or ultrasound, endoscopy, elastography, tactile imaging, and thermography.

Although two-dimensional (2D) techniques are still in wide use despite the advance of three-dimensional (3-D) tomography, specifically due to possible low cost and sometimes high resolution of 2D images, 3-D visualization forms the base of modern radiology. 3-D medical imaging is a revolutionary optical imaging technology that provides an enriched image of the interior body for medical analysis by utilizing 3-D imaging modalities. The technology has equipped healthcare professionals with the ability to access new angles, resolutions and details to provide a better anatomical overview while reducing radiation for patients. 3-D medical imaging provides enhanced images of blood vessels and better images of bones. The global 3-D medical imaging market has been prevalent in devices used for X-ray, ultrasound, MRI, and computer tomography scan (i.e. CT scan). Typically, 3-D visualization is often performed through a client viewer that must render images of the 3-D medical image volume in response to actions taken by a user, such as rotating or translating the viewpoint or applying different colorizations.

SUMMARY

A method for preemptively generating and rendering a view of a computerized image is provided. The method may include determining rendering parameters for the computerized image by predicting an action to be performed on the computerized image, wherein the action modifies a view of the computerized image, and wherein the determined rendering parameters are based on the modified view of the computerized image. The method may further include preemptively rendering the view of the computerized image that is based on the determined rendering parameters before the action is performed on the computerized image.

A computer system for preemptively generating and rendering a view of a computerized image is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include determining rendering parameters for the computerized image by predicting an action to be performed on the computerized image, wherein the action modifies a view of the computerized image, and wherein the determined rendering parameters are based on the modified view of the computerized image. The method may further include predictively rendering the view of the computerized image that is based on the determined rendering parameters before the action is performed on the computerized image.

A computer program product for preemptively generating and rendering a view of a computerized image is provided. The computer program product may include one or more computer-readable storage devices and program instructions stored on at least one of the one or more tangible storage devices, the program instructions executable by a processor. The computer program product may include program instructions to determine rendering parameters for the computerized image by predicting an action to be performed on the computerized image, wherein the action modifies a view of the computerized image, and wherein the determined rendering parameters are based on the modified view of the computerized image. The computer program product may include program instructions to preemptively render the view of the computerized image that is based on the determined rendering parameters before the action is performed on the computerized image.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
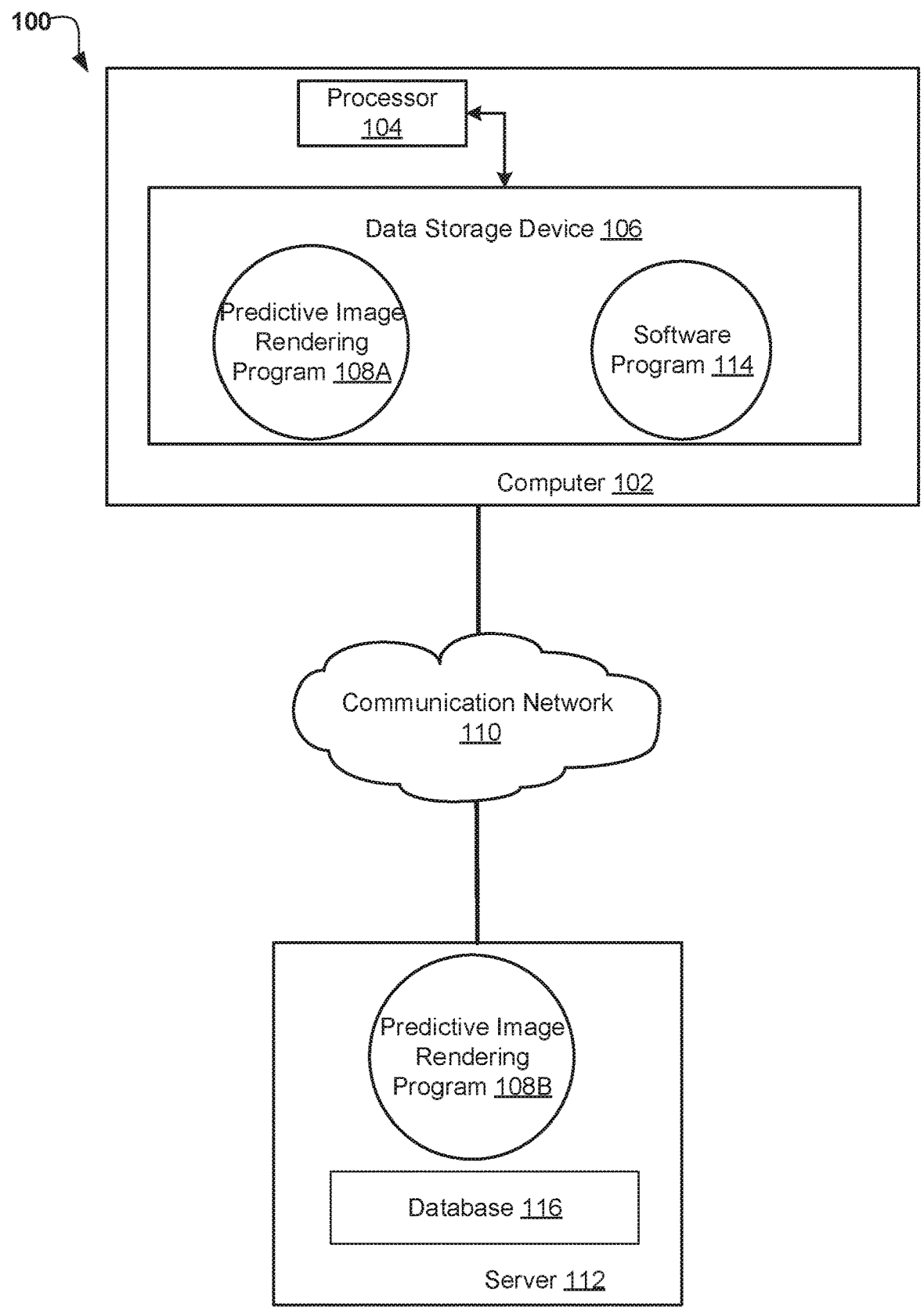
FIG. 1 illustrates a networked computer environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

As previously described, embodiments of the present invention relate generally to the field of computing, and more particularly, predictively rendering one or more views of an image on a client image viewer. Specifically, the present invention has the capacity to improve the technical field associated with computer imaging by predicting a next action or set of actions to be performed by a user on an image using a client imaging viewer, and in turn, may pre-emptively start a process for rendering an image that corresponds with the user's predicted next actions. More specifically, for example, and in relation to the field of healthcare, the present invention may identify and log a computer image (such as a 3-D image of an X-ray or CT scan), log a type of medical exam being performed by a user (such as a physician or medical personnel), and log actions taken by the user that pertain to the image and the type of exam (such as the user rotating the 3-D image to view different parts of a body). Then, in the future, the present invention may preemptively start a process for rendering different views and/or frames of an image that may correspond with a user's predicted next actions based on the previously logged data.

As previously described with respect to medical imaging, 3-D medical imaging is a revolutionary optical imaging technology that provides an enriched image of the interior body for medical analysis by utilizing 3-D imaging modalities. Typically, 3-D visualization is often performed through a client viewer that must render images of the 3-D medical image volume (and/or different frames of the 3-D medical image) in response to actions taken by a user, such as rotating or translating the viewpoint or applying different colorizations. Therefore, client 3-D medical imaging viewers must deliver images to the user in response to their actions as quickly as possible. Ideally the frame rate of image updates should match the refresh rate of the monitor, which is at least 60 hz for typical monitors and up to 240 hz for specialized monitors. However, 3-D image volume rendering is an expensive operation by itself, and the frame rate delivered by a client 3-D image viewer may be impacted by internet traffic, latency, and other factors when sending requests for images and receiving the images from a 3-D image rendering server. Specifically, for example, a command (such as rotating command) that a radiologist wants to execute on a 3-D image typically has to be sent to a cloud server, the cloud server then has to render the image, and finally the image has to be sent back and downloaded by the client viewer. Based on internet traffic, this overall process can either be impacted by lag or can cause lag between the movement of a user's mouse and the movement of the 3-D image on screen, which may not be close to meeting the refresh rate of the monitor Furthermore, due to limitations of current hardware, frame rates approaching the monitor refresh rate may be difficult, if not, impossible to achieve.

However, using machine learning and deep learning algorithms, the proposed method, computer system, and computer program product may address this issue by preemptively rendering images associated with a 3-D image on a client image viewer. Specifically, the method, computer system, and computer program product may predict a next action or set of actions to be performed by a user on an image using a client imaging viewer, and in turn, pre-emptively start a process for rendering a 3-D image that corresponds with the user's predicted next actions. More specifically, the method, computer system, and computer program may identify and continuously log an image as well as actions taken by the user that pertain to the image and that correspond to a type of exam (i.e. medical exam) being performed by the user. Then, in the future, the present invention may pre-emptively start a process for rendering different views and/or frames of an image that corresponds with a user's predicted next actions based on the logged data.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, an exemplary networked computer environment 100 in accordance with one embodiment is depicted. The networked computer environment 100 may include a computer 102 with a processor 104 and a data storage device 106 that is enabled to run a predictive image rendering program 108A and a software program 114, and may also include a microphone (not shown). The software program 114 may be an application program such as a image rending application and/or one or more mobile apps running on a client computer 102, such as a desktop, laptop, tablet, and medical device. The predictive image rendering program 108A may communicate with the software program 114. The networked computer environment 100 may also include a server 112 that is enabled to run a predictive image rendering program 108B and the communication network 110. The networked computer environment 100 may include a plurality of computers 102 and servers 112, only one of which is shown for illustrative brevity. For example, the plurality of computers 102 may include a plurality of interconnected devices, such as the mobile phone, tablet, and laptop, associated with one or more users.

According to at least one implementation, the present embodiment may also include a database 116, which may be running on server 112. The communication network 110 may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 3, server computer 112 may include internal components 800*a* and external components 900*a*, respectively, and client computer 102 may include internal components 800*b* and external components 900*b*, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a medical device, a mobile device, a telephone, a personal digital assistant, a netbook, a laptop computer, a tablet computer, a desktop computer, or any type of computing device capable of running a program and accessing a network. According to various implementations of the present embodiment, the predictive image rendering program 108A, 108B may interact with a database 116 that may be embedded in various storage devices, such as, but not limited to, a mobile device 102, a networked server 112, or a cloud storage service.

According to the present embodiment, a program, such as a predictive image rendering program 108A and 108B may run on the client computer 102 and/or on the server computer 112 via a communications network 110. The predictive image rendering program 108A, 108B may preemptively render and display views of an image on client computer 102. Specifically, a user using a client computer 102, which may include a computer imaging and display device, may run a predictive image rendering program 108A, 108B that may interact with a software program 114, such as a medical imaging application, to identify and continuously log an image and actions taken by the user on the client computer 102 that pertains to that image as well as pertains to a type of exam (i.e. medical exam) being performed by the user. Then, in the turn, the present invention may preemptively start a process for rendering different views of a similar or the same image based on the logged data.

Specifically, according to one embodiment, the predictive image rendering program 108A, 108B may detect a user's login credentials on the client computer 102. For example, the predictive image rendering program 108A, 108B may be running on client computer 102, and the predictive image rendering program 108A, 108B may detect that a user logs into client computer 102, where client computer 102 may include or is connected to an imaging device (not shown). More specifically, for example, the user may be a physician, and the physician may want to perform a computerized tomography scan (CT or CAT scan) of a patient's chest. Therefore, the user may log into a client computer 102 using login credentials, such as a username and password, which may be detected by the predictive image rendering program 108A, 108B. The client computer 102 may also include one or more machines for performing the CT scan. Specifically, the client computer 102 may include one or more computers and/or rotating X-ray machines to create cross-sectional images of the body. For example, during a CT scan, the patient may lie in a tunnel-like machine while the inside of the machine rotates and takes a series of X-rays from different angles. These pictures may then be sent to (from a server 112) and/or generated and displayed by the client computer 102, where the pictures may be combined to create images or cross-sections of the body or, more particularly, to produce a 3-D image of a particular area of the body. In turn, the predictive image rendering program 108A, 108B may produce a 3-D image of the patient's chest and may include a 3-D image viewer for viewing the 3-D image.

According to one embodiment, the predictive image rendering program 108A, 108B may also detect a type of exam that the user is performing. As previously described, the predictive image rendering program 108A, 108B may detect that the user logs into the client computer 102. Furthermore, with respect to the previous example, the predictive image rendering program 108A, 108B may detect that the user wants to perform a CT scan of a patient's chest. More specifically, according to one embodiment, the predictive image rendering program 108A, 108B may present a user interface on client computer 102 that includes different selectable options corresponding to different types of exams (i.e. exams of particular areas of the body) that the user may want to perform. For example, the predictive image rendering program 108A, 108B may include selectable options such as chest exam, leg exam, heart exam, back exam, etc. According to one embodiment, the different selectable options may also just list particular areas of the body that the user would like to examine such as chest, heart, back, etc. The predictive image rendering program 108A, 108B may enable a user to select one or multiple options. Therefore, the predictive image rendering program 108A, 108B may detect the type of exam that the user is performing based on the user's selection/action. In turn, the predictive image rendering program 108A, 108B may perform a CT scan of the particular area of the patient's body based on the options chosen by the user and/or the type of exam chosen by the user.

Also, according to one embodiment, the predictive image rendering program 108A, 108B may determine the type of exam the user is performing based on the particular part of the body that the user is viewing. For example, the predictive image rendering program 108A, 108B may provide an option to scan an entire body, and in response to the user selecting this option, the predictive image rendering program 108A, 108B may produce sets of 3-D images corresponding to different areas of a patient's body. Thus, the predictive image rendering program 108A, 108B may produce a 3-D image of the patient's chest, a 3-D image of the patient's leg, and other 3-D images corresponding to the rest of the patient's body. In turn, according to one embodiment, the predictive image rendering program 108A, 108B may enable the user to select which 3-D image the user wants to view on the 3-D image viewer that is associated with the predictive image rendering program 108A, 108B. For example, the user may choose to view the 3-D image associated with the patient's chest. As such, the predictive image rendering program 108A, 108B may detect that the user is performing a chest exam or that the user is simply viewing that particular part of the body.

Figure 2:
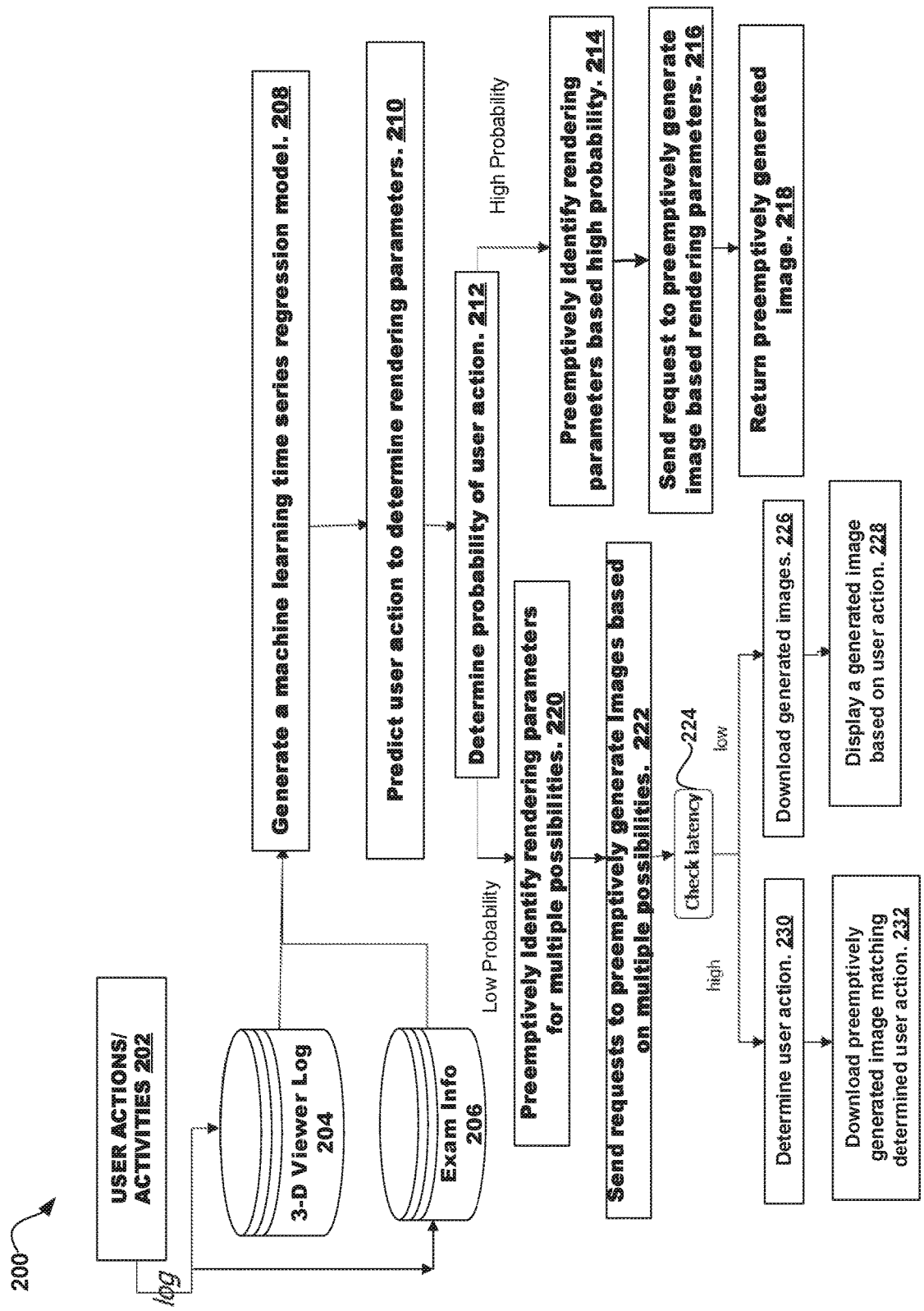
FIG. 2 is an operational flowchart illustrating the steps carried out by a program for preemptively generating and rendering a view of a computerized image according to one embodiment.

Referring now to FIG. 2, an operational flowchart illustrating the steps carried out by a program for preemptively rendering a view of an image is depicted. Specifically, at 204, the predictive image rendering program 108A, 108B may log user actions/activities 202 associated with an image using the 3-D viewer log 204 as well as a log which types of exams were viewed by which users using exam info 206. More specifically, for example, the 3-D viewer log 204 may include detailed records of user actions 202 such as when the user may have modified a viewpoint, changed colorization parameters, selected a tool, and any other actions that resulted in a request to a rendering server (such as server 112) for rendering new and/or different parameters or perspectives of an image. Furthermore, exam info 206 may log which types of exams were viewed by which users during the time the user perform the actions of modifying the viewpoint, changing colorization parameters, selecting a tool, etc. Therefore, the user actions logged by the 3-D viewer log 204 may be correlated with the type of exam logged by exam info 206 such that the predictive image rendering program 108A, 108B may determine which actions are performed during which exams and by which users. For example, a radiologist may want to perform a cardiac calcium score exam on a CT scan of a patient's chest whereby a 3-D image of the patient's chest is produced. Accordingly, the radiologist may first center the viewpoint of the 3-D image on the heart, and then the user may zoom in and rotate to view the coronary arteries. As such, the predictive image rendering program 108A, 108B may specifically log that during a cardiac calcium score exam, the user may perform such actions as first centering the 3-D image on the heart and then zooming in and rotating the 3-D image to view the coronary arteries.

According to one embodiment, and as described at 208, the predictive image rendering program 108A, 108B may use machine learning and/or deep learning techniques to interpret the logged data from the 3-D viewer log 204 and the exam info 206 to generate a time series regression model such that the data is in a series of particular time periods or intervals. Specifically, the predictive image rendering program 108A, 108B may use machine learning techniques—such as Hidden Markov models (HMM) and conditional random fields (CRF)—and/or deep learning techniques—such as recurrent neural networks (RNN), temporal convolutional network (TCN), and long short-term memory network (LSTM)—to produce a time series regression model (a combination of the machine learning and deep learning techniques). More specifically, the predictive image rendering program 108A, 108B may use the time series regression model to take time series data and predict a next element/action in the time series. Therefore, based on the 3-D viewer log 204 and exam info 206, the predictive image rendering program 108A, 108B may translate the user actions performed on a 3-D image during a certain type of exam into a series of actions. For example, a first logged action in the time series associated with a cardiac calcium score exam may be centering the 3-D image on the heart, then in a next minute a second logged action may be zooming in, and in the next 3 seconds a third logged action may be rotating the 3-D image to view the coronary arteries.

For each type of user action, new rendering parameters of the 3-D image (i.e. imaging parameters representing new/different viewpoints, colorizations, and/or states of the 3-D image) must be produced. Specifically, and as previously described, a command (such as a rotating command) that a user executes on a 3-D image typically has to be sent to a server, the server then has to render that view of the 3-D image by identifying the rendering parameters of the image that corresponds to the rotated view, and finally that view of the 3-D image has to be sent back and downloaded by the client computer 102. Based on such issues as network/internet traffic, this overall process can either be impacted by network/internet lag or can cause input lag between the movement of a user's mouse and the movement of the 3-D image on screen. Therefore, the predictive image rendering program 108A, 108B may automatically and continuously train and update the time series regression model to predict a next action by the user such that the rendering parameters of the 3-D image that are based on the next action are preemptively (or already) produced or in the process of being produced before the next action is performed. Specifically, the predictive image rendering program 108A, 108B may train and update the time series regression model based on previously performed user actions and exams.

Thereafter, and as described at 210, the predictive image rendering program 108A, 108B may use the time series regression model to predict a user action and determine the rendering parameters of an image that corresponds to the predicted user action. Specifically, the predictive image rendering program 108A, 108B may predict a user action to determine a state of a 3-D image of a certain type of exam based the type of exam being performed and based on previous user actions. For example, given a set of previously performed cardiac calcium score exams conducted by different users and the user actions associated with those exams on a 3-D image of a chest, the predictive image rendering program 108A, 108B may determine that a user likely first centers on the heart of the 3-D image during that exam, then the user is likely to zoom in and rotate the 3-D image to view the coronary arteries. The predictive image rendering program 108A, 108B may determine this likelihood based on a percentage, score, or threshold value, such as greater than 80% (i.e. given a certain type of exam, users performed a certain next user action on a 3-D image more than 80% of the time based on a current state or current viewpoint of the 3-D image). Thus, for example, based on the user choosing to perform a cardiac calcium score exam, the predictive image rendering program 108A, 108B may determine that the first action by the user is likely to be the user centering the 3-D image on the heart based on previous exams. Furthermore, based on the user centering the 3-D image on the heart, the predictive image rendering program 108A, 108B may determine that the next user action is likely to be the user rotating the image to view the coronary arteries.

According to one embodiment, the predictive image rendering program 108A, 108B may predict multiple user actions based on a current viewpoint and/or state of an image and/or based on the type of exam that is performed. For example, in response to the user choosing to perform a cardiac calcium score exam, the predictive image rendering program 108A, 108B may determine the next few actions that are likely to be performed by the user and/or all of the actions that are likely to be performed by the user on the 3-D image. As such, the predictive image rendering program 108A, 108B may interpret the 3-D viewer log 204 and exam info 206 as a time series in which the next action depends on the last one or more actions performed by the user, and/or depends on a current viewpoint and state of the 3-D image, and the likely next action or sequence of actions also depends on the type of exam being performed.

Thereafter, at 212, in response to predicting one or more user actions, the predictive image rendering program 108A, 108B may determine the probability of the one or more user actions to begin the process for preemptively generating the rendering parameters of an image that correspond to the predicted one or more user actions. More specifically, the predictive image rendering program 108A, 108B may preemptively generate the rendering parameters of the next user action based on a probability score. As previously described, the predictive image rendering program 108A, 108B may determine a likelihood of a next user action based on a percentage, score, or threshold value. For example, given a certain type of exam, the predictive image rendering program 108A, 108B may determine that users performed a certain next user action on a 3-D image more than 50% of the time based on a current state or current viewpoint of the 3-D image. Furthermore, according to one embodiment, that determined percentage and/or score may represent a probability score. Specifically, a probability score may represent a level of probability that the predictive image rendering program 108A, 108B has in a next action to be performed by a user and/or a next viewpoint and state corresponding to new rendering parameters of the 3-D image. For example, a score of 76% or better may represent a high probability score while a score below 76% may be regarded as a low probability score. According to one embodiment, the level of probability may be configurable such that different percentages may represent different probability scores or levels of probability. In turn, the predictive image rendering program 108A, 108B may use the probability to preemptively identify and generate a view (according to the determined rendering parameters) of a 3-D image based on predicted next user actions before those actions are performed by the user.

Accordingly, in response to the predictive image rendering program 108A, 108B determining a high probability score, the predictive image rendering program 108A, 108B may preemptively identify the rendering parameters of the image based on the probability of the predicted user action as depicted at 214. More specifically, the predictive image rendering program 108A, 108B may determine the next rendering parameters, such as determining that during a certain exam, the user will perform a rotate command to view a left side of a chest 3-D image, so the viewpoint of the left side of the 3-D image are the predicted/identified rendering parameters. Thereafter, at 216, the predictive image rendering program 108A, 108B may send a request to a server 112 to preemptively generate a view of the image that corresponds to the rendering parameters (i.e. generate the viewpoint of the left side of the 3-D image). Then, at 218, the server 112 may return the generated image based on the predicted user action and rendering parameters, and the predictive image rendering program 108A, 108B may download the generated images onto client computer 102 and, thus, be preemptively ready to present/display the generated view of the image before the user takes the corresponding action to view the left side of the chest.

According to one embodiment, in response to determining a high probability score, the predictive image rendering program 108A, 108B may also preemptively generate a sequence of next images based on a likely sequence of user actions. For example, and as previously described, in response to the user choosing to perform a cardiac calcium score exam, the predictive image rendering program 108A, 108B may determine the next few actions that are likely to be performed by the user and/or all of the actions that are likely to be performed by the user on the 3-D image during the exam. In turn, the predictive image rendering program 108A, 108B may send a request to the server 112 to generate views of the image corresponding to the rendering parameters for each of the next likely performed user actions. Then, at 218, the server 112 may return the generated images based on the predicted user actions and rendering parameters, and the predictive image rendering program 108A, 108B may present/display each of the generated views of the image before the user takes each corresponding predicted action.

Alternatively, the predictive image rendering program 108A, 108B may determine a low probability score. Specifically, for example, and as depicted at 220, the predictive image rendering program 108A, 108B may determine that there are 2 or more different and most likely possibilities (based on the probability score) of what a user may do next with regard to an image based on the type of exam and/or the current rendering parameters of the image. For example, for a given type of exam, a user may rotate a centered image to the left as a next action in 52% of cases when performing the exam or rotate the image to the right as a next action in 48% of cases. As such, at 220, the predictive image rendering program 108A, 108B may determine/predict that these actions and the rendering parameters for the image that are associated with these actions are the most likely possibilities, and therefore, may preemptively identify the rendering parameters for the image for each action—i.e. preemptively identify the rendering parameters resulting from the user rotating the image to the left and the rendering parameters resulting from the user rotating the image to the right. In turn, at 222, the predictive image rendering program 108A, 108B may send requests to the server 112 to preemptively generate images corresponding to the rendering parameters for each of the next likely performed user actions.

Furthermore, and as depicted at 224, in response to the server 112 returning the generated rendering parameters of the image (i.e. the generated images) based on the predicted next user actions, the predictive image rendering program 108A, 108B may check internet/network latency associated with a client computer 102 before determining to download the generated images on the client computer 102. For example, a server 112 may be used to preemptively generate the images corresponding to the rendering parameters and the server 112 may be located on-site with the client computer 102 (for example, in a same building or within a certain geographical vicinity), which may result in no latency issues, or the server 112 may be located at a different site than the client computer 102, which may increase the chances of latency issues. Thus, to reduce internet traffic and/or possible further latency issues, the predictive image rendering program 108A, 108B may perform a latency test at 224. In response to determining a low latency at 226 (i.e. a network and/or internet connection with a low time delay), the predictive image rendering program 108A, 108B may automatically download each of the preemptively generated images based on the predicted possibilities from step 222. Then, at 228, the predictive image rendering program 108A, 108B may display the one preemptively generated image in response to the user actual actually executing the predicted actions action that corresponds to the one preemptively generated image. For example, if the user performs the actual action of rotating the image to the left, based on the determined low latency, the predictive image rendering program 108A, 108B will have already automatically downloaded images resulting from both actions—i.e. the action of rotating the image to the left and to the right—to then be ready to display the one generated image corresponding to the user rotating the image to the left.

However, in response to the predictive image rendering program 108A, 108B determining a high latency (i.e. a network and/or internet connection with a high time delay), at 230, the predictive image rendering program 108A, 108B may wait to download a preemptively generated image from the multiple preemptively generated images that correspond to the predicted possibilities until determining the actual action executed by the user with regard to the image. For example, based on a determined high latency, the predictive image rendering program 108A, 108B may choose to observe what action the user actually performs before downloading a preemptively generated image (from the multiple preemptively generated image) that matches the user's actions at 232. For example, if the user performs the actual action of rotating the image to the left, the predictive image rendering program 108A, 108B may then download the preemptively generated image corresponding to that action—i.e. the view of the image resulting from a rotation to the left—and then display that preemptively generated image via client computer 102.

It may be appreciated that FIGS. 1-2 provide only illustrations of one implementation and does not imply any limitations with regard to how different embodiments may be implemented. Many modifications to the depicted environments may be made based on design and implementation requirements. For example, and as previously described, the predictive image rendering program 108A, 108B may predict a next user action based on a current viewpoint and state of an image and/or based on the type of exam that is performed. According to a further embodiment, the predictive image rendering program 108A, 108B may predict a next user action based on the current viewpoint and state, the type of exam that is performed, as well as based on which user is performing the action. More specifically, different users may perform a specific exam differently. For example, while a majority of users may perform certain actions with regard to a specific type of exam, one or more users may typically perform a different action. Furthermore, and as previously described, the predictive image rendering program 108A, 108B may determine which user is performing which actions based on login credentials. Therefore, the predictive image rendering program 108A, 108B may predict a next user action by placing more weight (scoring-wise) on the specific user performing a given type of exam over the type of exam itself, a feature that may be configurable by a user.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 3:
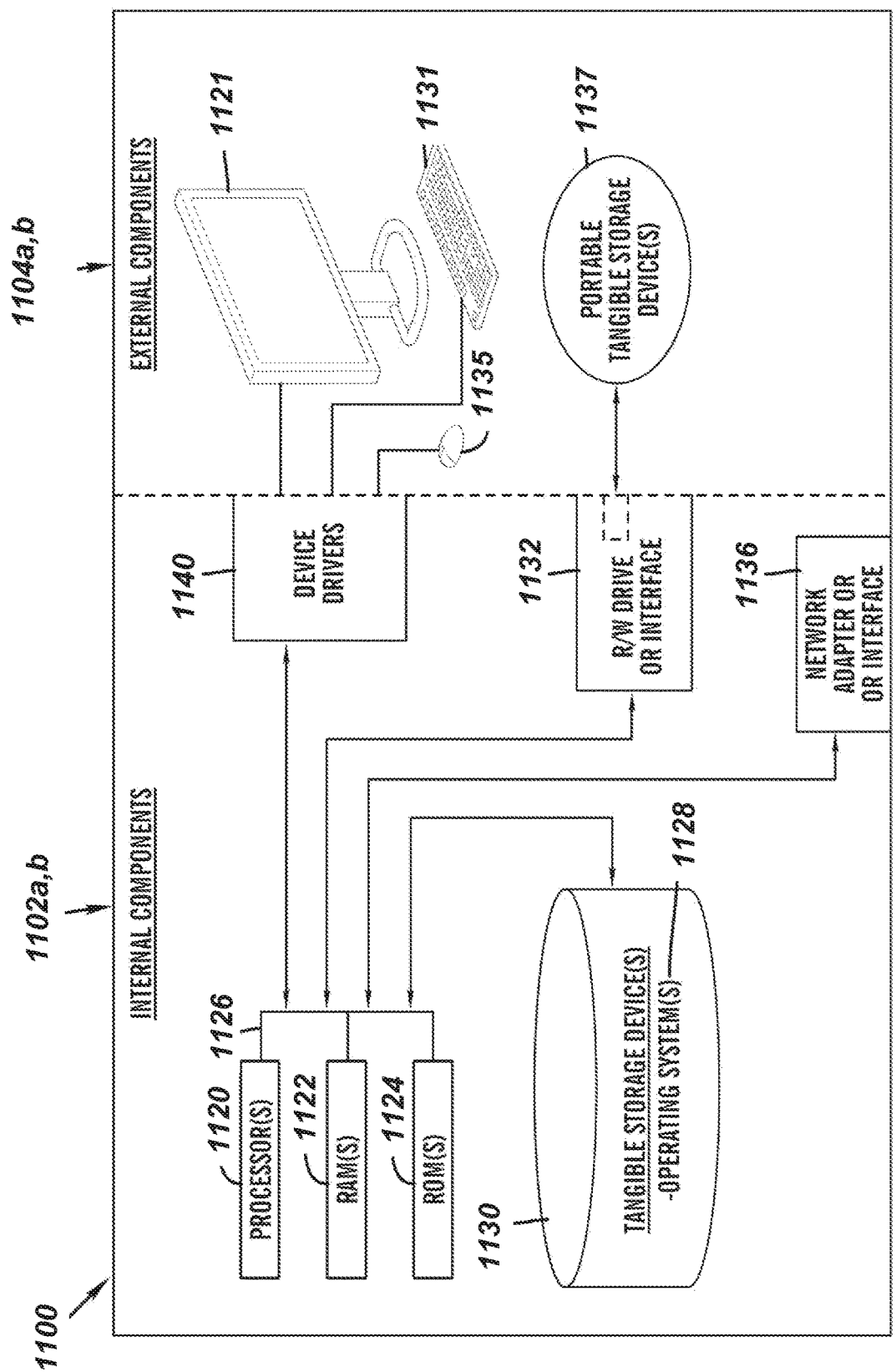
FIG. 3 is a block diagram of the system architecture of the program for preemptively generating and rendering a view of a computerized image according to one embodiment.

FIG. 3 is a block diagram 1100 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 1102, 1104 is representative of any electronic device capable of executing machine-readable program instructions. Data processing system 1102, 1104 may be representative of a smart phone, a computer system, PDA, or other electronic devices. Examples of computing systems, environments, and/or configurations that may represented by data processing system 1102, 1104 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) include respective sets of internal components 1102 a, b and external components 1104 a, b illustrated in FIG. 3. Each of the sets of internal components 1102 a, b includes one or more processors 1120, one or more computer-readable RAMs 1122, and one or more computer-readable ROMs 1124 on one or more buses 1126, and one or more operating systems 1128 and one or more computer-readable tangible storage devices 1130. The one or more operating systems 1128, the software program 114 (FIG. 1) and the predictive image rendering program 108A (FIG. 1) in client computer 102 (FIG. 1), and the predictive image rendering program 108B (FIG. 1) in network server computer 112 (FIG. 1) are stored on one or more of the respective computer-readable tangible storage devices 1130 for execution by one or more of the respective processors 1120 via one or more of the respective RAMs 1122 (which typically include cache memory). In the embodiment illustrated in FIG. 3, each of the computer-readable tangible storage devices 1130 is a magnetic disk storage device of an internal hard drive. Alternatively, each of the computer-readable tangible storage devices 1130 is a semiconductor storage device such as ROM 1124, EPROM, flash memory or any other computer-readable tangible storage device that can store a computer program and digital information.

Each set of internal components 1102 a, b, also includes a R/W drive or interface 1132 to read from and write to one or more portable computer-readable tangible storage devices 1137 such as a CD-ROM, DVD, memory stick, magnetic tape, magnetic disk, optical disk or semiconductor storage device. A software program, such as a predictive image rendering program 108A and 108B (FIG. 1), can be stored on one or more of the respective portable computer-readable tangible storage devices 1137, read via the respective R/W drive or interface 1132, and loaded into the respective hard drive 1130.

Each set of internal components 1102 a, b also includes network adapters or interfaces 1136 such as a TCP/IP adapter cards, wireless Wi-Fi interface cards, or 3G or 4G wireless interface cards or other wired or wireless communication links. The predictive image rendering program 108A (FIG. 1) and software program 114 (FIG. 1) in client computer 102 (FIG. 1), and the predictive image rendering program 108B (FIG. 1) in network server 112 (FIG. 1) can be downloaded to client computer 102 (FIG. 1) from an external computer via a network (for example, the Internet, a local area network or other, wide area network) and respective network adapters or interfaces 1136. From the network adapters or interfaces 1136, the predictive image rendering program 108A (FIG. 1) and software program 114 (FIG. 1) in client computer 102 (FIG. 1) and the predictive image rendering program 108B (FIG. 1) in network server computer 112 (FIG. 1) are loaded into the respective hard drive 1130. The network may comprise copper wires, optical fibers, wireless transmission, routers, firewalls, switches, gateway computers, and/or edge servers.

Each of the sets of external components 1104 a, b can include a computer display monitor 1121, a keyboard 1131, and a computer mouse 1135. External components 1104 a, b can also include touch screens, virtual keyboards, touch pads, pointing devices, and other human interface devices. Each of the sets of internal components 1102 a, b also includes device drivers 1140 to interface to computer display monitor 1121, keyboard 1131, and computer mouse 1135. The device drivers 1140, R/W drive or interface 1132, and network adapter or interface 1136 comprise hardware and software (stored in storage device 1130 and/or ROM 1124).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
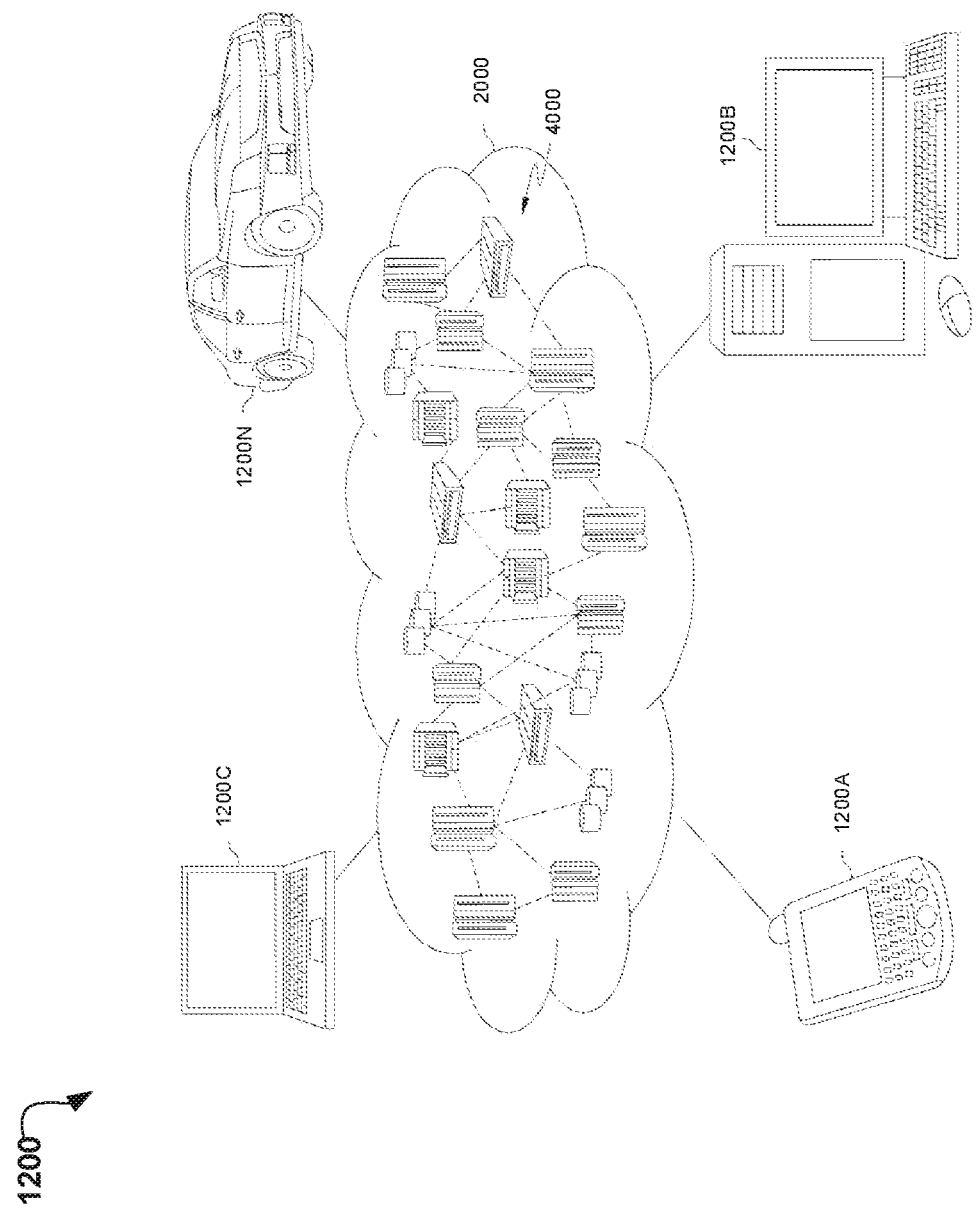
FIG. 4 is a block diagram of an illustrative cloud computing environment including the computer system depicted in FIG. 1, in accordance with an embodiment of the present disclosure.

Referring now to FIG. 4, illustrative cloud computing environment 1200 is depicted. As shown, cloud computing environment 1200 comprises one or more cloud computing nodes 4000 with which local computing devices used by cloud consumers, such as, for example, personal digital assistant (PDA) or cellular telephone 1200A, desktop computer 1200B, laptop computer 1200C, and/or automobile computer system 1200N may communicate. Nodes 4000 may communicate with one another. They may be grouped (not shown) physically or virtually, in one or more networks, such as Private, Community, Public, or Hybrid clouds as described hereinabove, or a combination thereof. This allows cloud computing environment 2000 to offer infrastructure, platforms and/or software as services for which a cloud consumer does not need to maintain resources on a local computing device. It is understood that the types of computing devices 1200A-N shown in FIG. 4 are intended to be illustrative only and that computing nodes 4000 and cloud computing environment 2000 can communicate with any type of computerized device over any type of network and/or network addressable connection (e.g., using a web browser).

Figure 5:
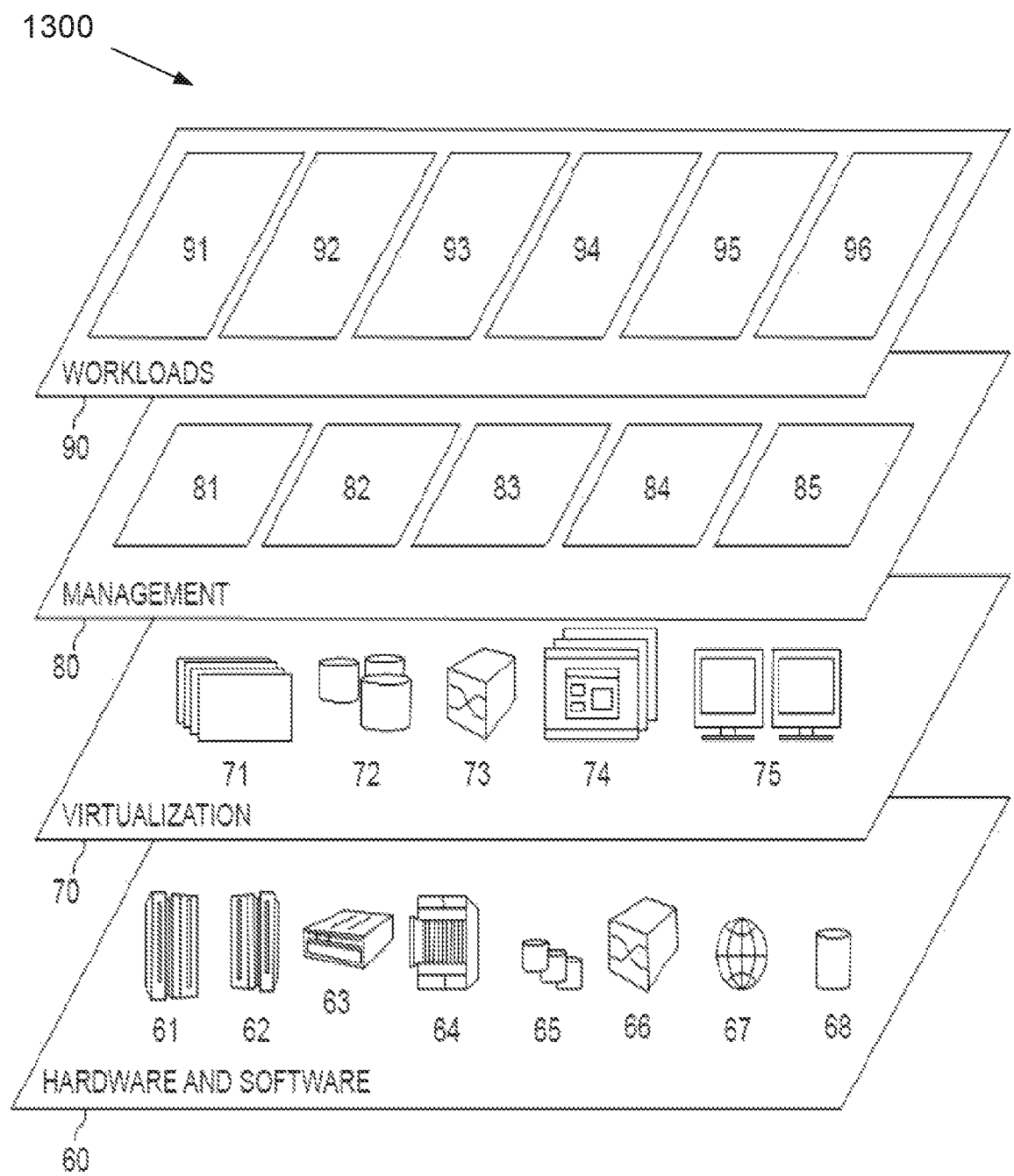
FIG. 5 is a block diagram of functional layers of the illustrative cloud computing environment of FIG. 4, in accordance with an embodiment of the present disclosure.

Referring now to FIG. 5, a set of functional abstraction layers 1300 provided by cloud computing environment 1200 (FIG. 4) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive image rendering 96. A predictive image rendering program 108A, 108B (FIG. 1) may be offered "as a service in the cloud" (i.e., Software as a Service (SaaS)) for applications running on computing devices 102 (FIG. 1) and may, on a computing device, preemptively generate and render a view of a computerized image.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for preemptively generating and rendering a view of a computerized image, the method comprising:

logging user actions performed on previous computerized images based on a specific user and based on a type of examination performed by the specific user;

correlating and associating the logged user actions with the specific user, the previous computerized images, and with the type of examination performed during the logged user actions;

determining rendering parameters for the computerized image by predicting an action to be performed on the computerized image based on a current viewpoint of the computerized image and the correlation between the logged user actions, the specific user, the computerized image, and the type of examination being performed, wherein the action modifies a view of the computerized image, and wherein the determined rendering parameters are based on the modified view of the computerized image; and preemptively rendering the view of the computerized image for the specific user based on the determined rendering parameters pertaining to the type of exam being executed before the action is performed on the computerized image.

2. The method of claim 1, wherein predicting the action to be performed on the computerized image further comprises:

predicting the action based on the type of examination being performed on the computerized image and based on previously performed actions that correspond to the type of examination.

3. The method of claim 1, wherein predicting the action to be performed on the computerized image further comprises:

determining a probability for the action based on a previously performed action on the computerized image.

4. The method of claim 1, further comprising:

predicting a plurality of actions based on a determined probability for the predicted plurality of actions;

determining a plurality of rendering parameters for the computerized image that correspond to each predicted action associated with the predicted plurality of actions; and preemptively rendering a plurality of views of the computerized image based on the determined rendering parameters that correspond to the predicted plurality of actions.

5. The method of claim 4, further comprising:

in response to a first determination based on network latency, automatically downloading from a server the preemptively rendered plurality of views of the computerized image for display onto a computer before a predicted action from the predicted plurality of actions is performed.

6. The method of claim 4, further comprising:

in response to a second determination based on network latency, downloading from a server a preemptively rendered view of the computerized image that is associated with the plurality of views of the computerized image for display onto a computer in response to a predicted action being performed from the predicted plurality of actions.

7. The method of claim 1, further comprising:

displaying the preemptively rendered view of the computerized image in response to the action being performed on the computerized image.

8. A computer system for preemptively generating and rendering a view of a computerized image, comprising:

one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:

logging user actions performed on previous computerized images by a specific user based on a type of examination being performed;

correlating and associating the logged user actions with the specific user, the previous computerized images, and with the type of examination performed during the logged user actions;

determining rendering parameters for the computerized image by predicting an action to be performed on the computerized image based on a current viewpoint of the computerized image and the correlation between the logged user actions, the specific user, the computerized image, and the type of examination being performed, wherein the action modifies a view of the computerized image, and wherein the determined rendering parameters are based on the modified view of the computerized image; and preemptively rendering the view of the computerized image for the specific user based on the determined rendering parameters pertaining to the type of exam being executed before the action is performed on the computerized image.

9. The computer system of claim 8, wherein predicting the action to be performed on the computerized image further comprises:

predicting the action based on the type of examination being performed on the computerized image and based on previously performed actions that correspond to the type of examination.

10. The computer system of claim 8, wherein predicting the action to be performed on the computerized image further comprises:

determining a probability for the action based on a previously performed action on the computerized image.

11. The computer system of claim 8, further comprising:

predicting a plurality of actions based on a determined probability for the predicted plurality of actions;

determining a plurality of rendering parameters for the computerized image that correspond to each predicted action associated with the predicted plurality of actions; and preemptively rendering a plurality of views of the computerized image based on the determined rendering parameters that correspond to the predicted plurality of actions.

12. The computer system of claim 11, further comprising:

in response to a first determination regarding network latency, automatically downloading from a server the preemptively rendered plurality of views of the computerized image for display onto a computer before a predicted action from the predicted plurality of actions is performed.

13. The computer system of claim 11, further comprising:
in response to a second determination regarding network latency, downloading from a server a preemptively rendered view of the computerized image that is associated with the plurality of views of the computerized image for display onto a computer in response to a predicted action being performed from the predicted plurality of actions.

14. The computer system of claim 8, further comprising:
displaying the preemptively rendered view of the computerized image in response to the action being performed on the computerized image.

15. A computer program product for preemptively generating and rendering a view of a computerized image, comprising:
one or more tangible computer-readable storage devices and program instructions stored on at least one of the one or more tangible computer-readable storage devices, the program instructions executable by a processor, the program instructions comprising:
program instructions to log user actions performed on previous computerized images by a specific user based on a type of examination being performed;
program instructions to correlate and associate the logged user actions with the specific user, the previous computerized images, and with the type of examination performed during the logged user actions;
program instructions to determine rendering parameters for the computerized image by predicting an action to be performed on the computerized image based on a current viewpoint of the computerized image and the correlation between the logged user actions, the specific user, the computerized image, and the type of examination being performed, wherein the action modifies a view of the computerized image, and wherein the determined rendering parameters are based on the modified view of the computerized image; and
program instructions to preemptively render the view of the computerized image for the specific user based on the determined rendering parameters pertaining to the type of exam being executed before the action is performed on the computerized image.

16. The computer program product of claim 15, wherein the program instructions to predict the action to be performed on the computerized image further comprises:
program instructions to predict the action based on the type of examination being performed on the computerized image and based on previously performed actions that correspond to the type of examination.

17. The computer program product of claim 15, wherein the program instructions to predict the action to be performed on the computerized image further comprises:
program instructions to determine a probability for the action based on a previously performed action on the computerized image.

18. The computer program product of claim 15, further comprising:
program instructions to predict a plurality of actions based on a determined probability for the predicted plurality of next actions;
program instructions to determine a plurality of rendering parameters for the computerized image that correspond to each predicted action associated with the predicted plurality of actions; and
program instructions to preemptively render a plurality of views of the computerized image based on the determined rendering parameters that correspond to the predicted plurality of actions.

19. The computer program product of claim 18, further comprising:
program instructions to, in response to a first determination regarding network latency, automatically download from a server the preemptively rendered plurality of views of the computerized image for display onto a computer before a predicted action from the predicted plurality of actions is performed.

20. The computer program product of claim 18, further comprising:
program instructions to, in response to a second determination regarding network latency, download from a server a preemptively rendered view of the computerized image that is associated with the plurality of views of the computerized image for display onto a computer in response to a predicted action being performed from the predicted plurality of actions.

* * * * *